(12) United States Patent
Jackson et al.

(10) Patent No.: US 10,281,487 B2
(45) Date of Patent: May 7, 2019

(54) PROBE SYSTEM DESIGNED FOR PROBING OF ELECTRONIC PARTS MOUNTED INTO APPLICATION OR TEST BOARDS

(71) Applicants: Michael Stanley Jackson, Reno, NV (US); Clint Andrew Waggoner, Dayton, NV (US)

(72) Inventors: Michael Stanley Jackson, Reno, NV (US); Clint Andrew Waggoner, Dayton, NV (US)

(73) Assignee: The Micromanipulator Company, LLC, Carson City, NV (US)

( * ) Notice: Subject to any disclaimer, the term of this patent is extended or adjusted under 35 U.S.C. 154(b) by 410 days.

(21) Appl. No.: 14/489,408

(22) Filed: Sep. 17, 2014

(65) Prior Publication Data

US 2015/0160262 A1 Jun. 11, 2015

Related U.S. Application Data

(60) Provisional application No. 61/879,073, filed on Sep. 17, 2013.

(51) Int. Cl.
*G01R 1/04* (2006.01)
*G01N 21/956* (2006.01)

(52) U.S. Cl.
CPC ............. *G01R 1/04* (2013.01); *G01N 21/956* (2013.01); *G01R 1/0491* (2013.01)

(58) Field of Classification Search
CPC ........ G01R 1/04; G01R 1/0491; G01N 21/00; G01N 21/956

(Continued)

(56) References Cited

U.S. PATENT DOCUMENTS 5,268,637 A 12/1993 Liken et al.
6,861,856 B2 3/2005 Dunklee et al.
(Continued)

FOREIGN PATENT DOCUMENTS

GB 2308454 6/1997

OTHER PUBLICATIONS http://www.signatone.com/products/probestations/h100_hybrid.asp.
(Continued)

*Primary Examiner* — Melissa J Koval
*Assistant Examiner* — Courtney G McDonnough
(74) *Attorney, Agent, or Firm* — Ian Burns; ATIP Law (57) ABSTRACT

Apparatus for facilitating analytical probing of a packaged electronic device is provided. The device may provide a test chamber that holds the device to be tested and provides an elevated or reduced temperature environment to conduct testing of the device at end-use application temperature levels. The apparatus includes a test chamber having perimeter walls and a configurable cover. The cover includes an adjustable position probe entry port or aperture that may be positioned to provide probe access to any point within the test chamber, and may comprise a cover with such positionable port or a plurality of overlapping plates such as a first plate with a cutout quadrant that can be oriented to expose any quadrant of the test chamber and a second plate with at least one probe entry port that can be situated in the cutout to provide the probe entry port above a desired test area of the electronic device. A height adjustable framework supported above the test chamber allows a probe manipulator to be brought into a required position to operate a probe through the probe entry port of the test chamber and into contact with the packaged electronics. A microscope is positionable above the probe manipulator to assist in place- (Continued)

ment of the probe. The apparatus is designed so that temperature controlled air may be provided to the test chamber to facilitate testing at elevated or reduced temperatures.

14 Claims, 7 Drawing Sheets

(58) Field of Classification Search
USPC .................................................... 324/754.08
See application file for complete search history.

(56) References Cited

U.S. PATENT DOCUMENTS

| | | | |
|---|---|---|---|
| 7,368,925 B2 | 5/2008 | Navratil et al. | |
| 7,479,796 B2 | 1/2009 | Corbin, Jr. et al. | |
| 7,688,062 B2 | 3/2010 | Nordgren et al. | |
| 7,737,713 B2 | 6/2010 | Stadler | |
| 8,497,693 B2 | 6/2013 | Kiesewetter et al. | |
| 2003/0042921 A1* | 3/2003 | Hollman | G01R 1/07392 324/750.14 |
| 2005/0156610 A1* | 7/2005 | Navratil | G01R 31/2831 324/754.23 |
| 2008/0042670 A1* | 2/2008 | Nordgren | G01R 31/2886 324/755.01 |
| 2010/0052716 A1* | 3/2010 | Lou | G01R 31/2886 324/754.01 |
| 2010/0052717 A1* | 3/2010 | Lou | G01R 31/2877 324/754.01 |
| 2014/0232424 A1 | 8/2014 | Richmond, II et al. | |
| 2014/0239991 A1 | 8/2014 | Teich et al. | |

OTHER PUBLICATIONS http://www.ee.cityu.edu.hk/~iclab/M150_BRO.pdf.
http://www.mbelectronique.fr/CMI_PMC200_SS.pdf.
http://www.rubion.rub.de/files/pdf/PM5_5_2000_small.pdf.
http://www.bu.edu/photonics/files/2012/06/PM5.pdf.
http://www.mbelectronique.fr/CMI_PLC50_SS.pdf.
Cascade Microtech, Inc. is a major competitor in this area.

* cited by examiner

PROBE SYSTEM DESIGNED FOR PROBING OF ELECTRONIC PARTS MOUNTED INTO APPLICATION OR TEST BOARDS

CROSS REFERENCE TO RELATED APPLICATIONS

This application claims priority to U.S. provisional patent application Ser. No. 61/879,073, filed 17 Sep. 2013, the contents of which is herein incorporated by reference.

FIELD OF THE INVENTION

The present invention relates to devices and methods for testing electronic elements and circuitry.

BACKGROUND

It is necessary, for purposes of analytical testing of semiconductor circuits and electronic components, to make physical contact to a circuit with a metal probe which can conduct electricity to and from the device. Tools or "analytical wafer probing systems" which are designed primarily to provide a platform to hold semiconductor wafers and support high precision mechanical or motorized control positioners (or commonly called "manipulators") with attached very sharp needle probes (or micro-probes) for the purpose of making such contact and conducting electricity to and from the semiconductor device are commonplace in the semiconductor industry.

The design focus of these analytical wafer probing systems has so far primarily been to conduct electrical testing on circuits in the "wafer" stage of semiconductor manufacturing, before they are placed into a "package". This "package" is a structure that supports the circuit and which contains frames, wires and contacts from the circuit which can be connected to components, wires or electrical sockets on an external printed circuit board or electronic appliance. Once packaged, the semiconductor circuit is typically referred to as a "packaged device". Packaged devices that have been opened up (exposing circuitry) are occasionally probed to test the individual device independently (physically and/or electrically) of other components that operate in conjunction with the device for use in its final application.

With the advent of more complicated and multi-function semiconductor circuits and the accompanying complexity of associated electronic circuits—memory, power supplies, logic and transmission circuits for example, the need do analytical probing testing on packaged devices which are mounted on "test" or "application" boards has become essential. This is so that tests may be conducted which include the impact of associated electronics and which are furthermore done under actual use conditions or as close to those conditions as possible, referred to as "mission mode".

Such mission mode testing of packaged devices has heretofore been done on an analytical probing system designed for wafers. This impacts the utility and limits the capability of the analytical probing application in several ways. What is required is an improved device and method for testing of electronic circuits, in particular packaged devices.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to conduct analytical probe testing on a packaged electronic device;

the ability to conduct full mission mode testing of a packaged electronic device;

the ability to conduct analytical probe testing at elevated or lowered temperatures; and the ability to move probes to any desired position on a packaged electronic device and to any desired position on its application board.

These and other advantages may be realized by reference to the remaining portions of the specification, claims, and abstract.

BRIEF DESCRIPTION OF ONE EMBODIMENT OF THE PRESENT INVENTION

In one aspect, there is provided an apparatus for facilitating analytical probing of a packaged electronic device. The apparatus may include a platform on which is disposed a test chamber. A framework supported above the platform may itself support at least one platen that is moveable on the framework to bring at least one probe manipulator into a required test position above the test chamber.

In one aspect, there is provided an apparatus for facilitating analytical probing of a packaged electronic device within a test chamber. The test chamber may comprise a mount for mounting the packaged electronic device and a cover plate arrangement that can be selectably configured to provide a probe entry port above a desired test area of the packaged electronic device or its application board. The test chamber may be provided with temperature controlled air to facilitate testing at different temperatures.

In one aspect, there is provided a method for analytical probing of a packaged electronic device. The packaged electronic device may be located within a test chamber. A cover plate for the test chamber may be placed over the test chamber, with the cover plate being selected and orientated so that a desired test area of the electronic device and/or its application board is exposed through a probe entry port. A probe manipulator may be moved into position above the test chamber and operated to bring a probe into contact with the desired test area of the electronic package and/or application board.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Mission mode testing of packaged devices has heretofore been done on an analytical probing system designed for wafers. This impacts the utility and limits the capability of the analytical probing application in several ways, the primary of which include the following:

A. The analytical probing systems designed primarily for wafers move the structure that typically holds the wafer, the "wafer chuck", underneath fixed position contact probe needles or "probes". The probes are supported on plates or "platens" which are also fixed in their position and therefore the wafer chuck moves underneath these platens.

Semiconductor wafers do not have attached wiring or cabling. Therefore, movement of a wafer is not difficult as cables need not be moved or "dragged" with the movement of the wafer. Application or test boards, in contrast, are large and have significant input and output cabling and wiring attached. There is no room for this cabling on an analytical wafer probing system because the area around the chuck must be kept clear of cabling to allow the chuck to move the entire width (left to right) and depth (front to back) of the wafer. Even if the application or test board is rested on the wafer chuck its position will be changed by any drag on the connecting cables, tilting the board or moving it laterally, thus making it difficult to place the probes into contact with a circuit on the application or test board and to keep it there in good ohmic contact for the duration of an electrical test.

B. Semiconductor wafers are very flat so they do not extend in height by more than a few millimeters. Therefore, movement of a wafer under probes or under the above described platens does not require much room between the chuck and the platens. Application or test boards, in contrast, are large and have components that rise a significant distance above the surface of the board (in some cases inches). As the chuck moves under the platens the distance between the chuck and platens is too small for tall components.

C. The analytical wafer probing systems designed primarily for wafers do not have any surrounding physical structure to support the interface cabling or support electronics required for "mission mode" testing. In mission mode testing support electronics must be connected to the device to be tested so actual use cases can be duplicated and so such a supporting physical structure is important.

D. The analytical probing systems designed primarily for wafers do not provide the range of positioning of the electrical probes required for the large areas which must be traversed across a test or application board to physically reach different devices with the electrical probes. The probes on an analytical wafer probing system are designed to stay in a relatively small range of position. It is desirable for mission mode testing on application or test boards that the probes be moved to the device to be tested, sometimes many inches in position, so that the application or test board itself, with all its support cabling and interface, need not be moved.

E. The analytical probing systems designed primarily for wafers do not provide any means for testing devices, which are embedded in or mounted on a test or application board, at lowered or elevated temperatures. Heating or cooling of the semiconductor wafer on an Analytical Wafer Probing System is accomplished through a heated or cooled wafer chuck which heats and cools the wafer through contact. Application or Test Boards are not flat so contact to a heated or cooled chuck is poor, and the materials that make up the boards, the sockets which hold the packaged devices and the package itself are poor thermal conductors. Use of a forced air system to heat or cool the device to be tested by blowing directly on the device creates turbulence that makes it difficult to place a probe and maintain good, low electrical noise contact of the probe during an electrical test. This makes it extremely difficult to heat or cool the device to be tested, to maintain it at a controlled temperature, and to elevate or lower the temperature of surrounding components and devices to duplicate the uniform thermal environment present in actual use. Therefore testing of packaged devices at elevated or lowered temperatures is not practical on analytical wafer probing systems.

F. An analytical probing system designed for wafers does not provide for a large range of stable positioning for a microscope. To test an application or test board, the microscope must be able to move to the location of the device to be tested.

The present invention is a probe system designed for probing of electronic parts mounted into application or test boards. It allows a device, in its use-case form and mounting configuration, on a full application or test board with all physical socketing and electronic support components in place, to be imaged, micro-probed and tested at temperatures above or below ambient room temperature.

By contrast, in various embodiments, the present invention provides apparatus for facilitating analytical probing of a packaged electronic device and includes a test chamber having perimeter walls and a configurable cover plate. The cover plate includes a first plate with a cutout quadrant that can be oriented to expose any quadrant of the test chamber. A second plate with at least one probe entry port can be situated in the cutout to provide the probe entry port above a desired test area of the electronic device. A height adjustable framework supported above the test chamber allows a probe manipulator to be brought into a required position to operate a probe through the probe entry port of the test chamber and into contact with the packaged electronics. A microscope is positionable above the probe manipulator to assist in placement of the probe. Temperature controlled air may be provided to the test chamber to facilitate testing at elevated or reduced temperatures.

The invention may have one or more of the following capabilities:

The invention is designed to hold the application or test board in a fixed position on a physically and thermally stable mount, and bring the probes to the device to be tested, instead of moving the device to be tested to the probes. Thus interface cabling is not disturbed.

The invention supports the application or test board and the device to be tested in a deep chamber which allows for tall surrounding components.

The invention has a base of a vibration isolated table which provides space for cables and test boxes in close proximity to the device to be tested and the chamber that holds the application or test board is positioned inside an outer frame which provides support and ports for the cabling and interface connections to the board.

The invention has long, movable platens with a large range of motion that allow High Precision Manipulators and probes to move to any part of the application or test board while the board and its interface cabling remain fixed.

The apparatus includes a thermal chamber that holds the device to be tested and its entire application or test board. The system makes use of the output of a forced air thermal system (not part of the present invention) to heat or cool the device to be tested, its full application or test board, and surrounding devices and components to a controlled temperature within this chamber. The thermal chamber provides a probe entry port and turbulence from the forced air system is minimized at the probe port so that probes may be precisely positioned on the device to be tested and so that stability of contact of an electrical micro-probe or probes to a feature on the device to be tested is maintained.

The apparatus provides extended positioning of a System Microscope using a highly stable "boom" design so that any device on the application or test board may be imaged. The invention microscope "boom" is highly stable to support a broad range of microscope types and magnifications.

Figure 1:
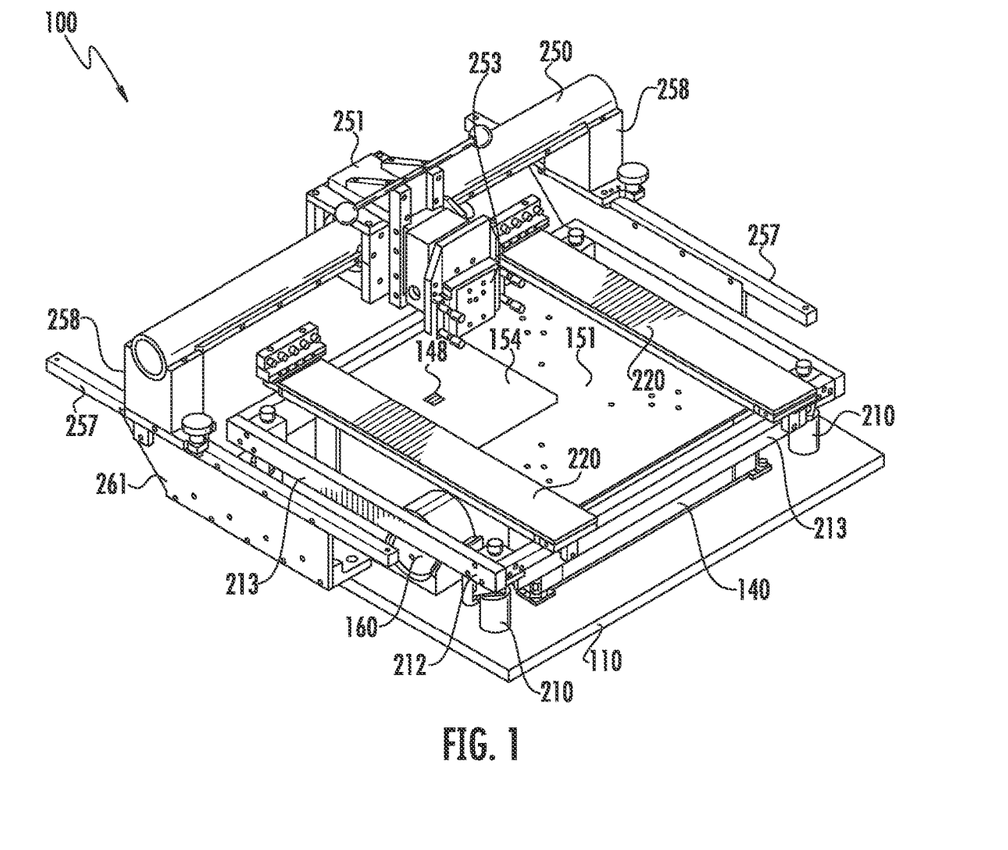
FIG. 1 is substantially a perspective view of a probe apparatus according to one embodiment of the present invention.

A probe system designed for probing of electronic parts, in particular for application or test boards, is depicted in perspective view generally at 100 in FIG. 1. The probe system 100 includes a platform means such as a table or platform 110 that provides a stable surface for supporting various components of the probe system. The platform 110 is depicted as approximately square though other shapes, including rectangular, circular, etc., may be employed.

Figure 2:
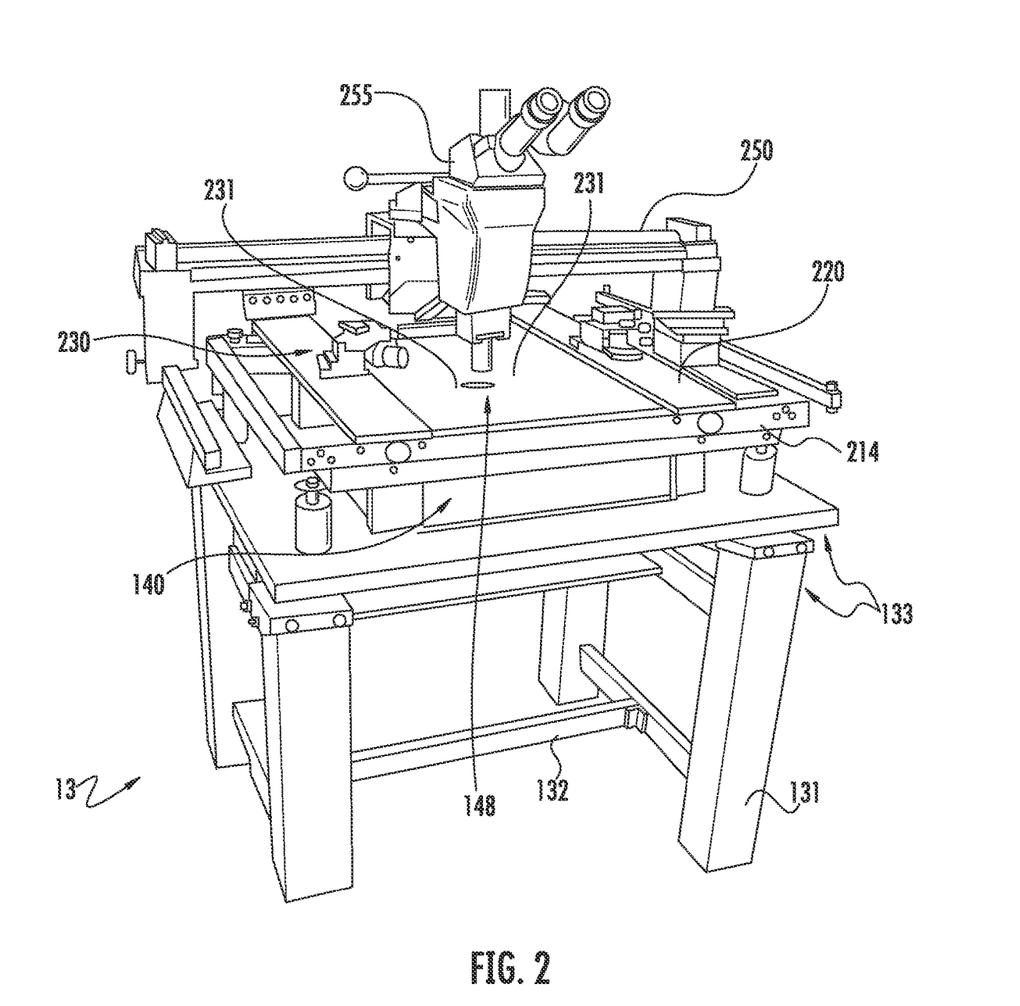
FIG. 2 substantially shows the probe apparatus on a vibration isolation table.

As shown in FIG. 2, the platform 110 may itself be built on a pneumatic vibration isolation table 13 that includes one or more legs 131, frame supports 132 and vibration isolating mounts 133. Various vibration isolating mounts may be utilized as will be apparent to the person skilled in the art.

Figure 3:
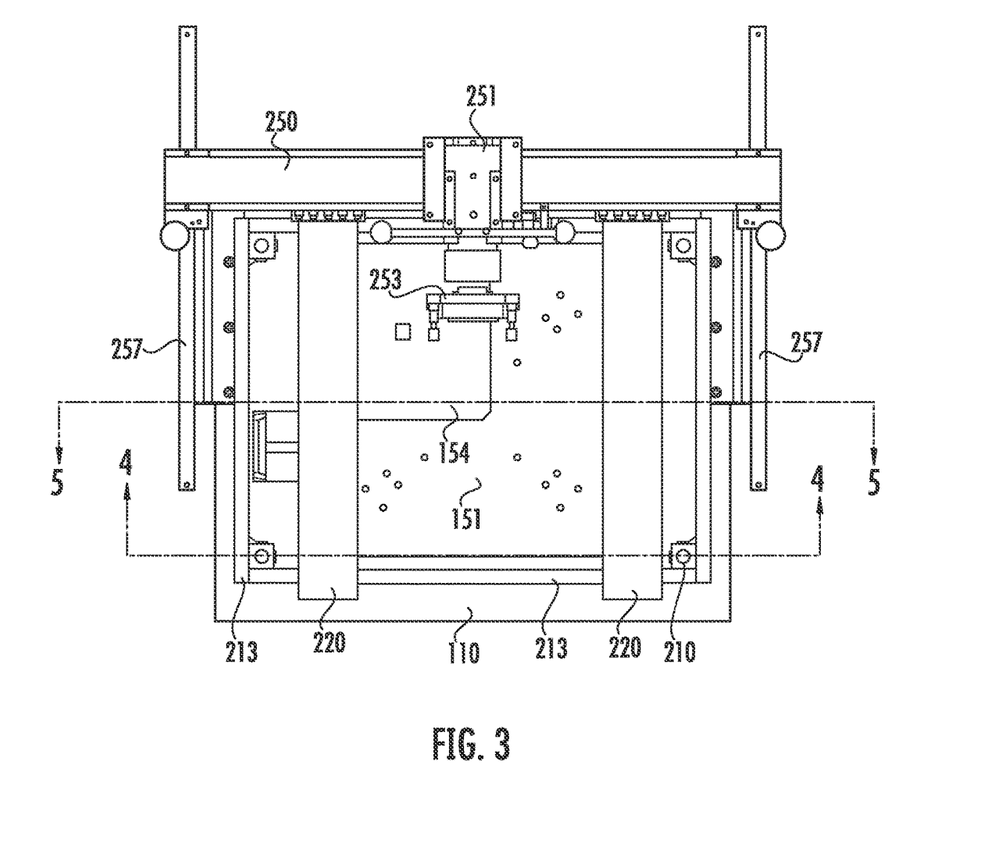
FIG. 3 is substantially a top view of the apparatus.
Figure 4:
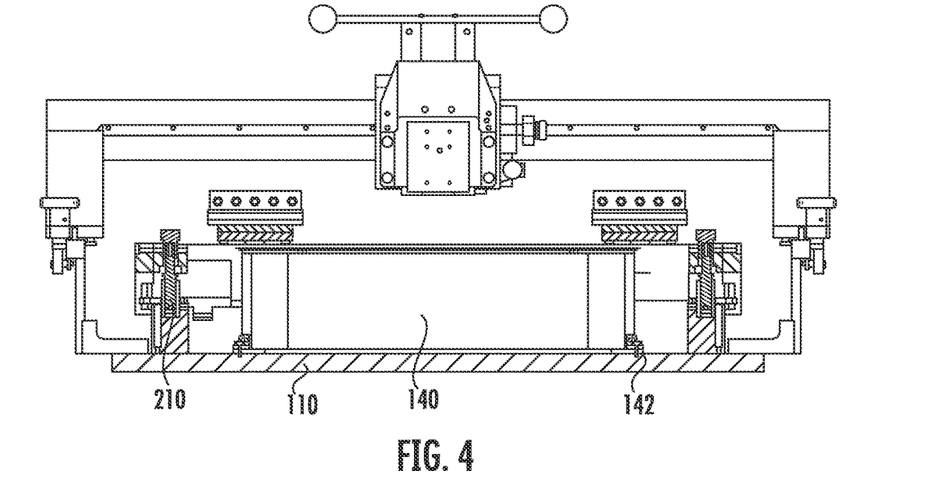
FIG. 4 substantially shows section A-A of FIG. 3.
Figure 5:
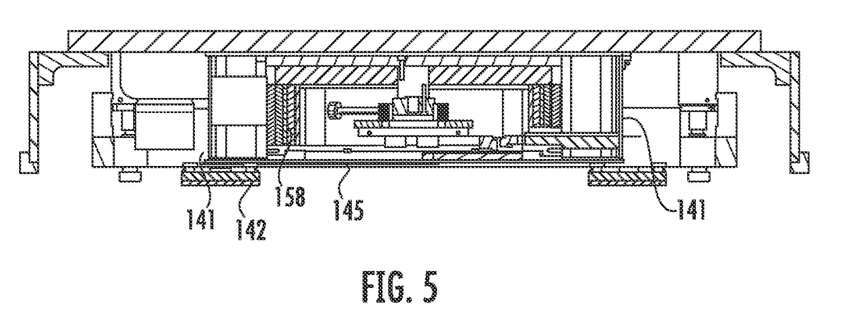
FIG. 5 substantially shows section B-B of FIG. 3.

FIG. 3 shows a top view of the probe system 100. FIG. 4 shows the section A-A of FIG. 3 while FIG. 5 shows the section B-B of FIG. 3.

Figure 6:
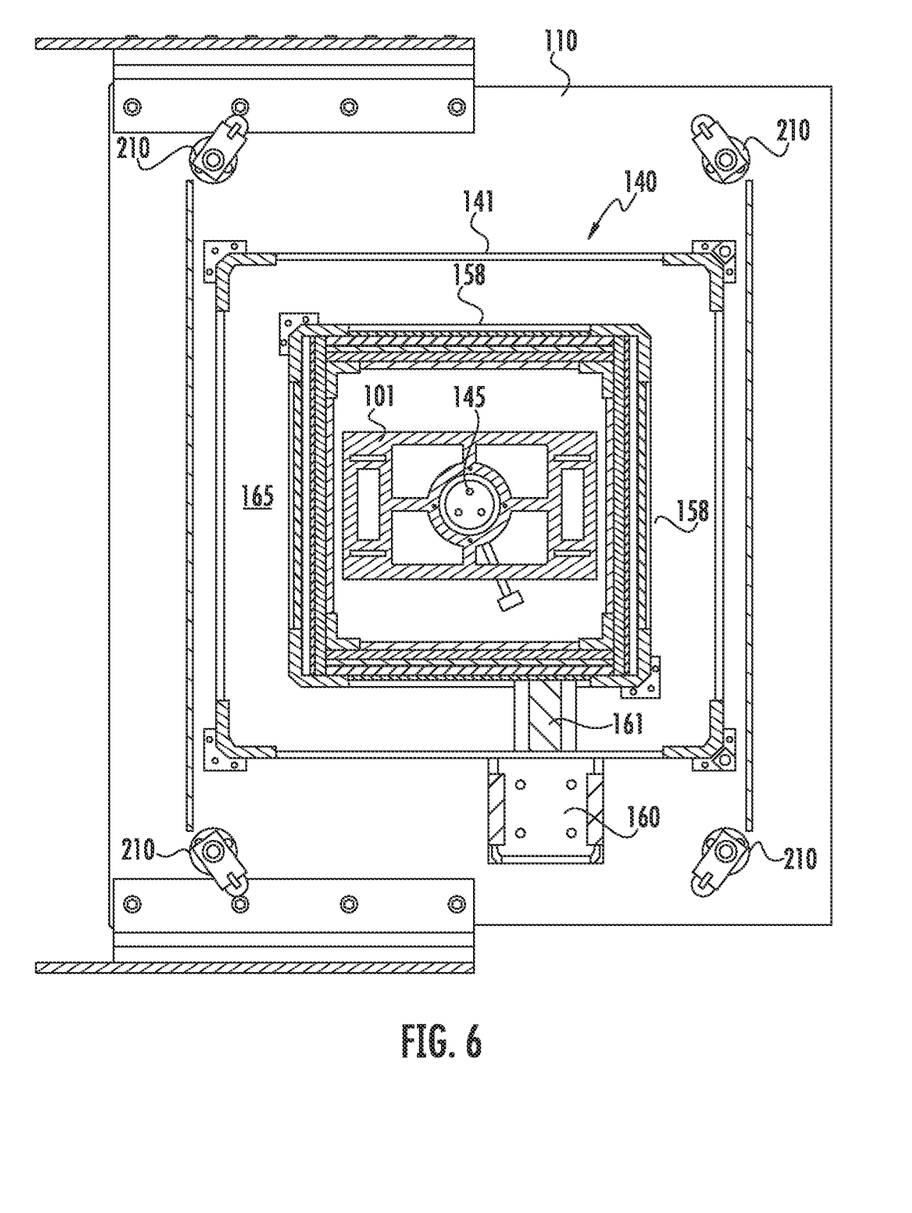
FIG. 6 substantially shows a section top view of the apparatus.

A thermal test chamber 140 is provided on the platform 110 and provides a test chamber means for and stably holding and isolating a packaged device or the like to be tested. The thermal test chamber is shown approximately centered on the platform 110 though may be disposed elsewhere on the platform 110. The thermal test chamber 140 is shown in more detail by the top cross section of FIG. 6. The thermal test chamber 140 includes a plurality of outer chamber walls 141 that form an outer perimeter that defines an internal cavity or chamber. The outer perimeter may be a square as shown or other shapes, including rectangles, circles, etc., may be employed. The chamber walls 141 may be made out of thermal insulating materials, including single materials, composite materials or multi-layered structures, as will be apparent to the person skilled in the art. An application or test board 101 may be located within the test chamber 140. The application or test board 101 may be supported on a thermal mount 145 that supports and thermally and/or electrically insulates the test board 101 from the platform 110. The height of the chamber walls 141 is sufficient to provide clearance above any components on the application or test board 101 as will be described in more detail below.

The chamber walls 141 may be supported by feet 142 that may be removably secured to the platform 110 by suitable attachments such as screws or the like.

The test chamber 140 may be closed from above by a cover plate means or arrangement. The cover plate arrangement may include a plurality of plates, at least one of which contains a probe entry port 148 through which micro-probes may be placed in contact with the device to be tested located within the test chamber 140.

Figure 7:
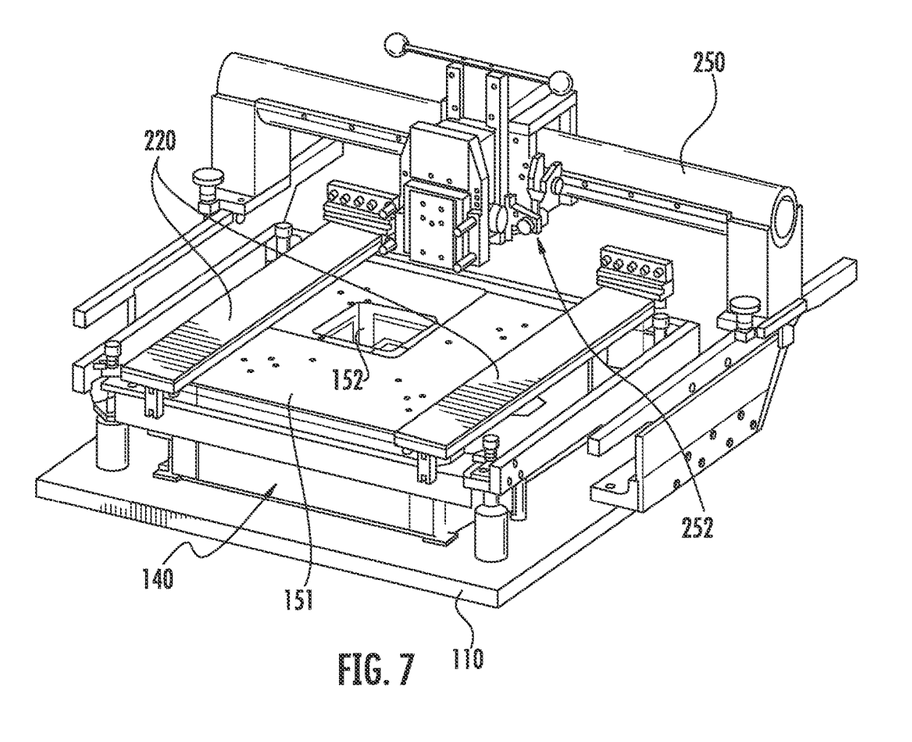
FIG. 7 substantially shows a perspective of the apparatus with second plate removed and exposed quadrant of the test chamber.

In one embodiment, the cover plate arrangement is designed to enable the plurality of plates to be arranged and combined to provide micro-probe access to any component or feature on the device to be tested, surrounding components or the application or test board 101. In one embodiment, the plate arrangement includes a first or main plate 151 with a large cutout designed to allow access to a single quadrant of the test chamber 140 at a time. FIG. 7 shows the first plate 151 with the cutout quadrant 152 exposed. The main plate 151 may be rotated and flipped through various orientations to change the quadrant of access. The main plate may sit within a lip or recess created by the chamber walls 141 of the test chamber 140.

A second, smaller plate 154 may be designed to fit within the cutout 152 of the main plate 151. The second plate 154 may include a probe entry port 148 that provides access from above for a probe to the test chamber 140 below the second plate 154. Various second plates 154 may be provided with probe entry ports in different locations depending on the test site of the board under test. By including only a small probe entry port or ports where required, the temperature within the test chamber 140 may be better controlled.

Heated or cooled forced air is introduced into the test chamber 140 via a forced air inlet 160. The inlet 160 may be connected to a supply (not shown) of heated or cooled air as required by suitable connections such as hoses, pipes, etc. The supplied air may be filtered or unfiltered.

A plurality of partitions 158 may be located within the test chamber 140 to surround the test board. The forced air may be supplied from the air inlet 160 via a connection 161 to the partitions 158. From there, the air may circulate around the partitions and through apertures in the partitions which prevent turbulence in the central test area where the probes are deployed. Minimizing turbulence in the probe area serves to ensure the accuracy of the probe placement.

A space 165 may be provided between the partitions 158 and the test chamber walls 141 to locate any peripheral devices and components required for proper mission testing of the board under test. Additional ports may be provided in the partitions for interface cabling and rigid interfaces.

The test chamber 140 may be removable from the platform 110 and replaceable with a test chamber of different size, shape, height or configuration as required by the board or packaged device under test.

The probe system also includes probe support means. The probe support means may include a framework supported above the test chamber 140 by a plurality of support posts 210. Four corner posts 210 are shown (FIG. 3) though a greater or lesser number of support posts may be utilized. The support posts 210 support a test facility frame means, e.g. framework 212, which may include frame members 213 on each side to create a four sided framework. More or less frame members 213 may be provided depending on test requirements. The support posts 210 that support the framework 212 may include precision adjustment to control the height of the framework 212 and thus the clearance of the framework 212 above the test chamber 140. Height adjustment may be by means of manual adjustment, e.g. threaded elements, or may be automated adjustment, such as by stepper motors within the support posts 210.

The framework 212 supports platens 220 that are slide, roll or otherwise traverse along one or more framework members 213 and that extend across two opposite framework members 213. Screw clamps 214 may be used to secure the platens 220 in their desired position on the framework members. Holes may be provided in the sides of the framework members for receiving the screw clamps or the clamps 214 may include plates that press against the framework members 213.

The moveable platens 220 are rigid support platforms for high precision manipulators 230 which hold micro-probes 231. The platens 220 are adjustable in plane to allow the probes to be positioned at any point over the device to be tested or its supporting application or test board 101 and neighboring components.

The manipulators 230 provide high precision control to the placement of microprobes 231. Many manipulators 230 and microprobes 231 are commercially available and the specific manipulator or microprobe is not considered to be pertinent to the present invention.

The platform 110 also includes microscope support means for stably supporting a microscope above the test chamber 140 over a large range of allowable motion. In one embodiment, the microscope support means may include a plurality of rails 257 mounted on opposite sides of the platform 110. As shown in FIG. 1, the rails 257 may be mounted outward of the platform 110 via angle brackets 261. The boom 250 is supported on the rails 257 by sliding supports 258 that slide, roll or otherwise traverse the rails 257 and can be clamped in position on the rails 257 to lock the position of the boom 250. The boom 250 extends between the opposed sliders 258 to traverse the area above the test chamber 140. A bracket 251 may be slidable or otherwise moveable on the microscope boom 250 and may be clamped in the desired position by clamps or the like. A microscope mount 253 is attached to the bracket 251 and provides a mount for a microscope 255. The microscope mount 253 contains fine positioning controls 252 (FIG. 7) with a limited range for locating very small features on the device to be tested. The specific microscope is not considered pertinent to the present invention and thus any of a wide variety of microscopes may be employed.

The boom 250 extends perpendicular to the rails 257 so that the position of the microscope 255 in one horizontal direction is controlled by the position of the microscope bracket 251 on the boom and in the orthogonal horizontal direction by the location of the slider brackets 258 on the rails 257. The length of the rails 257 is sufficient to enable the microscope 255 to traverse the entire dimension of the test chamber 140 to view any testable location of the test chamber 140.

Figure 8:
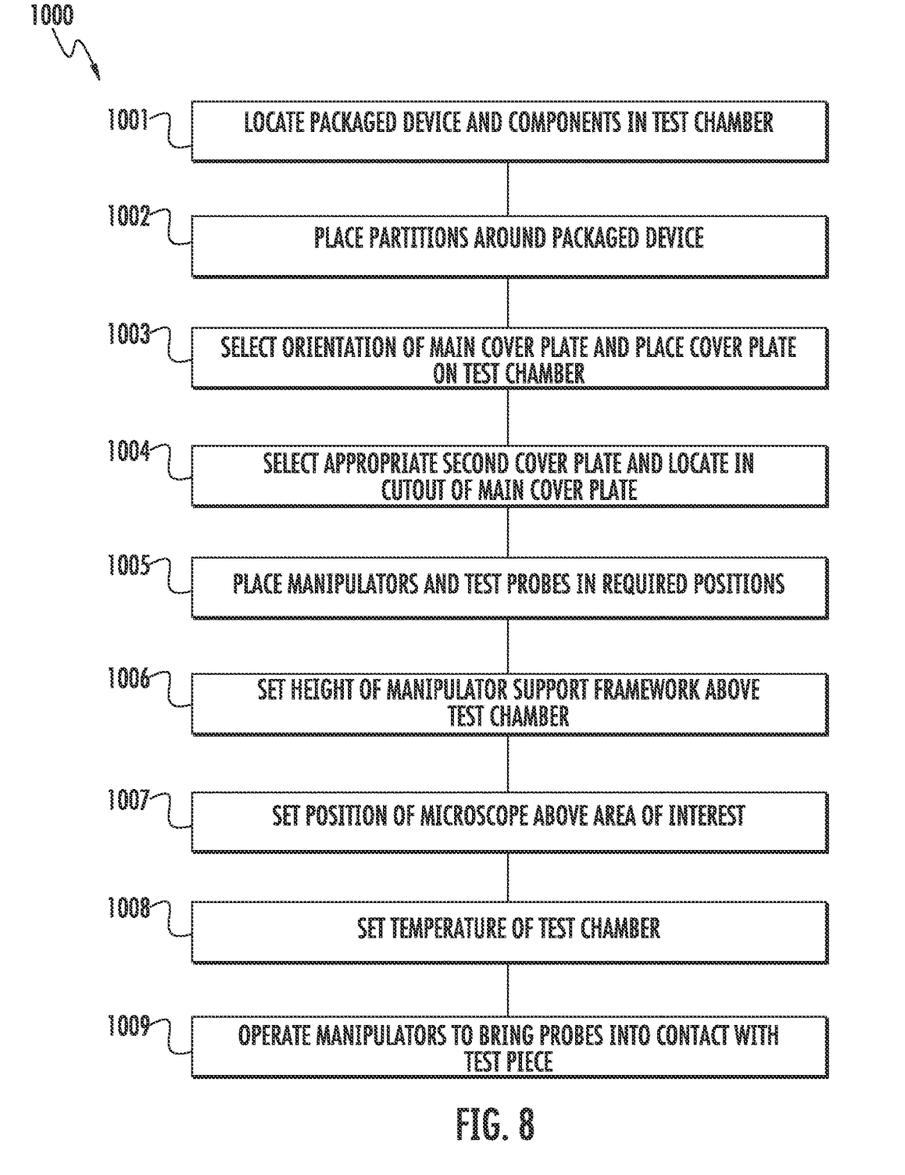
FIG. 8 substantially depicts a method for analytical probing of a packaged electronic device.

A method for mission testing of a packaged device is depicted in the flowchart 1000 of FIG. 8. At step 1001, the packaged device may be located with any of its peripheral devices, cabling and connections within the test chamber 140. The application or test board 101 of the packaged device is located on the thermal mount. At step 1002, partitions may be placed around the application or test board with through ports for cabling and interface connections to the peripheral components and devices. At step 1003, the main cover plate is orientated and place so that the open quadrant of the main plate is located above the application or test board, or other component to be probed. At step 1004, a second plate with an appropriately located probe entry port is selected and place in correct orientation within the main plate cutout.

At step 1005, the macro-positions of the manipulators of the test facility may be set by adjusting the position of the moveable platens on their respective framework supports and by locating the manipulators on the platens. At step 1006, the height of the framework may be adjusted by the adjustment posts 210.

At step 1007, the macro-positions of the microscope of the test facility may be set by adjusting the position of the microscope on the boom and by adjusting the position of the boom on the support rails.

At this stage, the test facility is fully configured and the actual testing may commence.

Testing may commence by directing temperature controlled air from a supply through forced air inlet to raise or lower the temperature within the test chamber 140 (step 1008). Manipulators 230 may be used to control the position of microprobes through the probe entry port(s) to bring the probes into contact with the element to be tested (step 1009). Vision through the microscope can aid in accurately locating the microprobes. Bringing the probe into contact with the element of the packaged device to be tested may include lowering the framework that supports the manipulator to move the probe toward the test piece within the test chamber.

In one specific example, the test facility and test chamber described herein can be used to test for faulty memory blocks on a new design of a PC solid state drive (SSD). The SSD contains multiple components, memory, power supply, and input/output devices all mounted on a printed circuit board (application board). Failures that present based on power supply tolerances and output demand can only be observed and located when the entire application board is exercised. The fault must be isolated by testing internally on the memory device using micro-probes. The invention supports such an application board in a stable position to allow for micro-probing and thus fault isolation.

The fault may further require elevated or lowered temperature to present. The fault may not present when only the memory device temperature is altered, as it may be associated with temperature-dependent impedance of the interconnection between the memory device and support components (i.e. the power supply). The invention allows the entire application board to be elevated or lowered in temperature with true use-case connections to external devices in place so that the fault may present, and be located, verified and isolated through micro-probing.

Although the description above contains many specifications, these should not be construed as limiting the scope of the invention but as merely providing illustrations of some of the embodiments of this invention. Thus, the scope of invention should be determined by the appended claims and their legal equivalents rather than by the examples given.

What is claimed is:

1. Apparatus for facilitating analytical probing of a packaged electronic device, the apparatus comprising:
   (A) a platform;
   (B) a test chamber disposed on the platform, the test chamber configured to receive and secure the packaged electronic device in a fixed position within the test chamber, the test chamber comprising at least one open probe entry port that provides a passage for at least one probe;

(C) a framework supported above the platform outside of the test chamber; and (D) at least one platen mounted on the framework outside of the test chamber, the at least one platen configured to support at least one probe manipulator above the test chamber, wherein the at least one platen is moveable on the framework to a selectable position to place a supported probe manipulator in a test position.

2. The apparatus of claim 1 wherein the framework is supported above the platform by a plurality of supports comprising height adjustment that adjusts the separation between the framework and the platform.

3. The apparatus of claim 1 wherein the framework comprises a pair of opposed frame members, the apparatus comprising a plurality of clamps that secure opposed ends of the at least one platen to a respective opposed frame member, wherein the clamps are moveable along their respective frame member.

4. The apparatus of claim 1 comprising a microscope support structure that supports a microscope above the test chamber, wherein the microscope support structure is moveable above the test chamber to enable a microscope supported by the microscope support structure to be moved to a position to view a selectable test area of the test chamber.

5. The apparatus of claim 4 wherein the microscope support structure comprises:

(A) a pair of opposed rails;

(B) a boom extending between the pair of opposed rails, the boom mounted to the pair of opposed rails to enable the boom to travel along the rails to a selectable position above the test chamber; and (C) a bracket for securing a microscope to the boom, wherein the bracket is able to travel along the boom to a selectable position on the boom.

6. The apparatus of claim 1 wherein the test chamber comprises:

(A) one or more walls that define a perimeter of the test chamber;

(B) a mount within the perimeter for mounting the packaged electronic device; and (C) a cover plate arrangement for covering the test chamber.

7. The apparatus of claim 6 wherein the cover plate arrangement comprises:

(A) a first plate comprising a cutout, the first plate able to be mounted on the test chamber in a plurality of orientations that alter the position of the cutout above the test chamber; and (B) a second plate configured to be received in the cutout, the second plate comprising at least one probe entry port.

8. The apparatus of claim 1 comprising an air inlet for providing temperature controlled air to the test chamber.

9. Apparatus for facilitating analytical probing of a packaged electronic device, the apparatus comprising:

(A) a platform;

(B) a test chamber disposed on the platform, the test chamber configured to receive and secure the packaged electronic device, the test chamber comprising:

(a) one or more walls that define a perimeter of the test chamber;

(b) a mount for mounting the packaged electronic device in a fixed position within the test chamber; and (c) a cover plate arrangement for covering the test chamber, the cover plate arrangement comprising:

(i) a first plate comprising a cutout, the first plate able to be mounted on the test chamber in a plurality of orientations that alter the position of the cutout above the test chamber; and (ii) a second plate configured to be received in the cutout, the second plate comprising at least one open probe entry port; and (C) at least one support for supporting at least one probe manipulator above and outside of the test chamber.

10. The apparatus of claim 9 wherein the test chamber comprises:

(A) one or more partitions within the perimeter of the test chamber;

(B) a space between the one or more partitions and the perimeter of the test chamber; and (C) wherein the space is configured to receive one or more peripheral components of the packaged electronic device necessary for conducting a mission mode test of the packaged electronic device.

11. The apparatus of claim 10 wherein the one or more partitions include one or more ports that enable one or more connections to be made from the peripheral components of the packaged electronic device.

12. The apparatus of claim 9 comprising an air inlet for providing temperature controlled air to the test chamber.

13. The apparatus of claim 9 comprising a framework supported above the platform, wherein the framework supports at least one platen that supports the at least one probe manipulator, wherein the platen is selectably moveable on the framework to adjust the position of the at least one probe manipulator above the test chamber.

14. The apparatus of claim 13 wherein the framework is supported above the platform by one or more height adjustable supports.

* * * * *